(12) United States Patent
Southall et al.

(10) Patent No.: US 8,278,359 B2
(45) Date of Patent: Oct. 2, 2012

(54) COMPOSITIONS CONTAINING AMINES AND USE THEREOF TO TREAT ACNE OR REDUCE THE APPEARANCE OF OIL OR PORES ON THE SKIN

(75) Inventors: Michael Southall, Lawrenceville, NJ (US); Katharine Martin, Ringoes, NJ (US); Elvin R. Lukenbach, Flemington, NJ (US); Binoy K. Bordoloi, Bridgewater, NJ (US); Menas Kizoulis, Union, NJ (US); Apostolos Pappas, Hillsborough, NJ (US); Catherine Stubler Salerno, Millington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 1054 days.

(21) Appl. No.: 11/351,865

(22) Filed: Feb. 10, 2006

(65) Prior Publication Data
US 2007/0042010 A1 Feb. 22, 2007

Related U.S. Application Data

(63) Continuation-in-part of application No. 11/312,984, filed on Dec. 20, 2005, which is a continuation-in-part of application No. 11/223,032, filed on Sep. 9, 2005, which is a continuation-in-part of application No. 11/066,362, filed on Feb. 25, 2005, now abandoned.

(51) Int. Cl.
A61K 8/42 (2006.01)
A61K 31/13 (2006.01)

(52) U.S. Cl. ........................................ 514/669; 424/401
(58) Field of Classification Search .................. 514/669; 424/401
See application file for complete search history.

(56) References Cited

U.S. PATENT DOCUMENTS

| | | | |
|---|---|---|---|
| 2,697,118 A | 12/1954 | Lundsted et al. | |
| 3,463,862 A | 8/1969 | Mazza | |
| 3,471,624 A | 10/1969 | Youngblood | |
| 3,862,309 A | 1/1975 | Krochock | |
| 3,916,008 A | 10/1975 | Green et al. | |
| 4,056,611 A | 11/1977 | Young | |
| 4,321,167 A | 3/1982 | Schmolka | |
| 4,511,563 A | 4/1985 | Schmolka | |
| 4,749,507 A | 6/1988 | Varco | |
| 4,778,825 A | 10/1988 | Smith et al. | |
| 4,822,604 A | 4/1989 | Knoll et al. | |
| 4,873,265 A | 10/1989 | Blackman | |
| 5,013,545 A * | 5/1991 | Blackman et al. | 514/716 |
| 5,554,647 A | 9/1996 | Perricone | |
| 5,621,088 A | 4/1997 | Gruber | |
| 5,643,586 A | 7/1997 | Perricone | |
| 5,700,455 A | 12/1997 | Hinterwaldner et al. | |
| 5,879,684 A | 3/1999 | Fox | |
| 5,879,690 A | 3/1999 | Perricone | |
| 5,925,337 A | 7/1999 | Arraudeau et al. | |
| 5,997,885 A * | 12/1999 | Koulbanis et al. | 424/401 |
| 6,086,863 A | 7/2000 | Ritter et al. | |
| 6,379,702 B1 | 4/2002 | Lorenz et al. | |
| 6,413,526 B1 | 7/2002 | Bazin et al. | |
| 2003/0026820 A1 | 2/2003 | De Lacharriere et al. | |
| 2003/0206958 A1 | 11/2003 | Cattaneo et al. | |
| 2003/0215476 A1 | 11/2003 | Cassin et al. | |
| 2004/0009140 A1 | 1/2004 | Nishijima et al. | |
| 2004/0101566 A1 * | 5/2004 | Cooper et al. | 424/489 |
| 2004/0136937 A1 | 7/2004 | Cassin | |
| 2005/0089486 A1 | 4/2005 | Spindler et al. | |

FOREIGN PATENT DOCUMENTS

| | | |
|---|---|---|
| DE | 202004006865 U | 12/2004 |
| EP | 0 023 978 A2 | 2/1981 |
| EP | 0 613 682 A1 | 9/1994 |
| EP | 0 755 671 B1 | 1/1997 |
| EP | 862914 A2 | 9/1998 |
| EP | 1 192 940 A | 4/2002 |
| EP | 1 216 969 A | 6/2002 |
| GB | 1 513 053 | 6/1978 |
| JP | 07/165560 A | 6/1995 |
| JP | 07/206680 A | 8/1995 |
| JP | 11/035445 A | 2/1999 |

(Continued)

OTHER PUBLICATIONS

Guidance for Industry, Container Closure Systems for Packaging, Human Drugs and Biologics (U.S. Department of Health and Human Services Food and Drug Administration, May 1999).*
Webster (Clinical Review, Acne vulgaris, BMJ vol. 325, Aug. 31, 2002, pp. 475-479).*
John A. Wenninger, G.N. McEwen, Jr.,International Cosmetic Ingredient Dictionary and Handbook, (1997), 1626, 1650-1667,1673-1686, 1693-1697,Seventh Edition 1997, vol. 2, The Cosmetic, Toiletry, and Fragrance Association, Washington, DC.
M. V. Bhide et al., Investigation into the Mechanism of Stimulation of Macrophages by Quadrol, Immunopharmacology and Immunotoxicology, vol. 9, No. 1, 1987, pp. 129-141.

(Continued)

*Primary Examiner* — San-ming Hui
*Assistant Examiner* — Kathrien Cruz

(57) ABSTRACT

The present invention features compositions comprising at least one compound of the formula I or formula II:

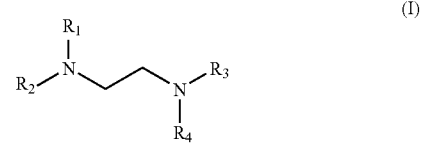

(I)

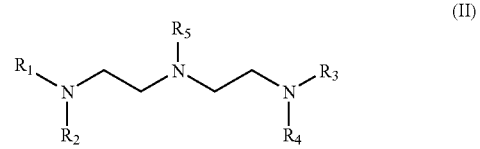

(II)

wherein R1, R2, R3, R4, and R5 independently, are selected from the group consisting of hydrogen, $C_1$-$C_6$ alkyl, $C_1$-$C_6$ hydroxyalkyl, or a cosmetically acceptable salt thereof, and the use thereof for treating acne and reducing the appearance of oil or pores on the skin.

2 Claims, No Drawings

FOREIGN PATENT DOCUMENTS

| | | | |
|---|---|---|---|
| JP | 11 269096 A | 10/1999 | |
| JP | 2002/529388 A | 9/2001 | |
| JP | 2002/515898 A | 5/2002 | |
| JP | 2002-212045 | 7/2002 | |
| JP | 2003/513895 A | 4/2003 | |
| JP | 2004-2289 | 1/2004 | |
| JP | 2004/131431 A | 4/2004 | |
| JP | 2004/524335 A | 8/2004 | |
| WO | WO 94/21221 A1 | 9/1994 | |
| WO | WO 95/27474 A1 | 10/1995 | |
| WO | WO 96/19180 A1 | 6/1996 | |
| WO | WO 97/33560 A | 9/1997 | |
| WO | WO 99/51213 A | 10/1999 | |
| WO | WO 00/24378 A1 | 5/2000 | |
| WO | WO 00/74699 | * | 12/2000 |
| WO | WO 00/74699 A | 12/2000 | |
| WO | WO 01/70132 A2 | 9/2001 | |
| WO | WO 02/19981 A2 | 3/2002 | |
| WO | WO 03/026680 A | 4/2003 | |
| WO | WO 03/086342 A1 | 10/2003 | |

OTHER PUBLICATIONS

M. Rajadhyaksha et al., In Vivo Confocal Scanning Laser Microscopy of Human Skin II: Advances in Instrumentation and Comparison with Histology, The Journal of Investigative Dermatology, vol. 113, No. 3, 1999, pp. 293-303.

I. Giaever et. al., Micromotion of mammalian cells measured electrically, Proc. Natl. Acad. Sci., vol. 88, 1991, pp. 7896-7900.

J. Wegener et al., Electric Cell-Substrate Impedance Sensing (ECIS) as a Noninvasive Means to Monitor the Kinetics of Cell Spreading to Artificial Surfaces, Experimental Cell Research, vol. 259, 2000, pp. 158-166.

M.V. Bhide et al., In Vitro Stimulation of Macrophages by Quadrol [N, N, N, N-Tetrakis(2-Hydroxypropyl)Ethylenediamine), Journal of Immunopharmacology, vol. 7 No. 3,1985, pp. 303-312.

Data sheet "How to put KYAMER™" PC to work for you, publicly available prior to Feb. 25, 2005.

Brisaert, M.G., Chemical Stability of tretinoin in dermatological preparations, Pharmaceutica Acta Helvetiae 70(1995) pp. 161-166.

Bhide, M.V., Promotion of Wound Collagen Formation in Normal and Diabetic Mice by Quadrol, Immunopharmacology and Immunotoxicology, 10(4), 1988,pp. 513-522.

Oriflame Intimate Wipes, Oriflame India Ltd, Jul. 4, 2005.

Oriflame Maxium Treatment Cream, Silver Oak Pvt. Ltd., Apr. 18, 2005.

Consentido Antibacterial Gel, Rene Desses de Venezuela C.A., May 2, 2005.

Dr. Fischer Botanics Anti-Perspirant/Deodorant Cream-Almond Milk; Aloe-Vera; Chamomile; Anti-Perspirant/Deodorant Gel—Almond Milk; Aloe-Vera; Chamomile; Anti-Perspirant/Deodorant Roll-On—Almond Milk; Aloe-Vera; Chamomile; Anti-Perspirant/Deodorant Spray—Almond Milk; Aloe-Vera; Chamomile; Anti-Perspirant/Deodorant Stick—Almond Milk; Aloe-Vera; Chamomile, Fischer Pharmaceuticals, Apr. 18, 2005.

Sundown Kids Color Bloqueador Solar—Uva FPS 30, Johnson & Johnson Industrial Ltda., Dec. 20, 2004.

Schwarzkopf Taft Style & Fix Gel to Go—Ultra Strong, Schwarzkopf & Henkel, Mar. 1, 2004.

FDS Pursonals Feminine Deodorant Spray—Extra Strength; White Blossom, Alberto-Culver USA, Inc., Jul. 22, 2002.

Becca Fine Loose Finishing Powder—Mocha; Eggshell; Bisque; Sesame; Ginger; Wheat; Spice; Cinnamon; Nutmeg; Carob; Crème Blush—Turkish Rose; Terracotta; Byzantine; Translucent CheekTint—Berry Compact Pressed Powder Bronzer—Lambada; Salsa; Calypso; Compact Fine Pressed Powder—Eggshell; Bisque; Sesame; Ginger; Nutmeg; Carob; Wheat; Moca; Spice; Cinnamon; Loose Shimmer Powder—Angel; Nymh; Hyawatha; Mermaid; Princess; Gypsy; Aphrodite; Pressed Shimmer Powder—Angel; Nymph; Aphrodite; Hyawatha; Princess; Gypsy; Mermaid, Cosmetic Developments Limited, Feb. 11, 2002.

Becca Crème Blush, Cosmetic Developments Limited, Nov. 26, 2004.

Becca Translucent Cheek Tint, Cosmetic Developments Limited, Nov. 26, 2004.

Becca Pressed Bronzing Powder, Cosmetic Developments Limited, Nov. 26, 2004.

Becca Fine Pressed Powder, Cosmetic Developments Limited, Nov. 26, 2004.

Becca Loose Shimmer Powder, Cosmetic Developments Limited, Nov. 26, 2004.

Becca Pressed Shimmer Powder, Cosmetic Developments Limited, Nov. 26, 2004.

Efraim Aisen et al, Sebum and Water Content in the Skin of Aged Immobilized Patients, Acta Derm Venereol (Stockh), 1997; vol. 77: pp. 142-143.

Mary Ellen Stewart et al, Suppression of Sebum Secretion with 13-cis-Retinoic Acid: Effect on Individual Skin Surface Lipids and Implications for Their Anatomic Origin, The Journal of Investigative Dermatology, 1984, vol. 82, No. 1, pp. 74-78.

Richard S. Greene et al, Anatomical Variation in the Amount and Composition of Human Skin Surface Lipid, The Journal of Investigative Dermatology, 1970, vol. 54, No. 3, pp. 240-247.

Anthony J.Thody et al., Control and Function of Sebaceous Glands, Physiological Reviews, vol. 69, No. 2, Apr. 1989, pp. 383-416.

Katsuyoshi Chiba et al, Changes in the Levels of Glutathione after Cellular and Cutaneous Damage Induced by Squalene Monohydroperoxide, J Biochem Molecular Toxicology, 2001, vol. 15, No. 3, pp. 150-158.

Apostolos Pappas, Metabolic Fate and Selective Utilization of Major Fatty Acids in Human Sebaceous Gland, The Society for Investigative Dermatology, Inc., Sep. 10, 2001, pp. 164-171.

Alan R. Shalita, et al., Effects of Tazarotene 0.1% Cream in the Treatment of Facial Acne Vulgaris:Pooled Results from Two Multicenter, Double-Blind, Randomized, Vehicle-Controlled, Parallel-Group Trials, Clinical Therapeutics, 2004, vol. 26, No. 11, pp. 1865-1873.

R. Ruy et al., The Organ-Maintained Human Sebaceous Gland, Dermatology, 1998, vol. 196, pp. 16-20.

Johnson & Johnson Consumer Companies, Inc., U.S. Appl. No. 11/066,362, filed Feb. 25, 2005.

Johnson & Johnson Consumer Companies, Inc., U.S. Appl. No. 11/223,032, filed Sep. 9, 2005.

Johnson & Johnson Consumer Companies, Inc., U.S. Appl. No. 11/312,984, filed Dec. 20, 2005.

Johnson & Johnson Consumer Companies, Inc., U.S. Appl. No. 11/351,862, filed Feb. 10, 2006.

Johnson & Johnson Consumer Companies, Inc., U.S. Appl. No. 11/066,631, filed Feb. 25, 2005.

Flick (Cosmetic and Toiletry Formulations, Second Edition, vol. 1, 1989, p. 816, ISBN 081551218X).

Guidance for Industry, Container Closure Systems for Packaging, Human Drugs and Biologics (US Department of Health and Human Services Food and Drug Administration, May 1999).

* cited by examiner

COMPOSITIONS CONTAINING AMINES AND USE THEREOF TO TREAT ACNE OR REDUCE THE APPEARANCE OF OIL OR PORES ON THE SKIN

CROSS REFERENCE TO RELATED APPLICATION

This is a continuation-in-part of application Ser. No. 11/312,984, filed Dec. 20, 2005, which is a continuation-in-part of Ser. No. 11/223,032, filed Sep. 9, 2005, which is a continuation-in-part of Ser. No. 11/066,362, filed Feb. 25, 2005 now abandoned, all of which are hereby incorporated by reference in their entirety.

BACKGROUND OF THE INVENTION

N,N,N',N'-tetrakis (2-hydroxypropyl)ethylenediamine has been disclosed for use as a catalytic agent. For example, PCT Patent Application No. WO/0170132 describes the use of N,N,N',N'-tetrakis(2-hydroxypropyl)ethylenediamine as catalytic agent to polymerize micropsheres prior to injection into the skin. Injection of microspheres into the skin acts to augment skin contour deficiencies such as wrinkles. The use of tertiary amines, such as N,N,N',N'-tetrakis(2-hydroxypropyl)ethylenediamine, as chelating agents to prevent the reduction of the salicylic acid is described in U.S. Pat. No. 4,822,604.

The application of N,N,N',N'-tetrakis(2-hydroxypropyl) ethylenediamine in cosmetic products has been described in European Patent No. 0023978 whereby the development of carcinogenic nitrosamines in cosmetic and toiletry products which contain triethanolamine is avoided by using N,N,N', N'-tetrakis(2-hydroxypropyl)ethylenediamine to neutralize acidic formulations. U.S. Pat. No 4,749,507 describes the use of N,N,N',N'-tetrakis(2-hydroxypropyl)ethylenediamine, for removing hair dyes from hair and skin and U.S. Pat. No. 3,916,008 describes the use of esters of ethylene diamine are useful as hypocholesterolaemic agents in animals and man. Bhide M V et al., Immunopharmacol. 1985;7(3):303-312 reported that treating macrophages in culture with N,N,N',N'-tetrakis(2-hydroxypropyl)ethylenediamine resulted in an increased macrophage activation, a pro-inflammatory response.

The present invention relates to the unexpected discovery that certain amine compounds, such as N,N,N',N'-tetrakis(2-hydroxypropyl)ethylenediamine, are topically effective for treating signs of aging, discoloration and/or puffiness around the eye, inflammation of skin, acne, reducing the appearance of oil or pores on the skin, and/or darkening the skin. Furthermore, it was also unexpectedly discovered that such amine compounds also have the ability to potentiate the activity of other cosmetically active agents.

SUMMARY OF THE INVENTION

In one aspect, the present invention features a method of (i) treating at least one sign of aging on the skin selected from the group consisting of enhancing the elasticity of said skin, enhancing the firmness of said skin, and reducing the appearance of wrinkles or cellulite on the skin, (ii) treating inflammation, such as non-acne inflammation of skin, (iii) reducing the appearance of discoloration or puffiness around the eye, (iv) treating acne, (v) reducing the appearance of oil or pores on the skin, and/or (vi) darkening the skin by administering to skin in need of such treatment a composition comprising at least one compound of the formula I or formula II described below.

In another aspect, the present invention features a product containing (a) a composition including at least one compound of the formula I or formula II described below and (b) instructions directing the user to apply said composition to skin in order to (i) treat at least one sign of aging on the skin selected from the group consisting of enhancing the elasticity of said skin, enhancing the firmness of said skin, and reducing the appearance of wrinkles on the skin, (ii) treat inflammation, such as non-acne inflammation of skin, (iii) reducing the appearance of discoloration or puffiness around the eye, (iv) treat acne, (v) reducing the appearance of oil or pores on the skin, and/or (vi) darkening the skin.

In another aspect, the present invention also features a method of promoting a composition including at least one compound of the formula I or formula II described below, wherein said method comprises directing the user to apply said composition to skin in order to (i) treat at least one sign of aging on the skin selected from the group consisting of enhancing the elasticity of said skin, enhancing the firmness of said skin, and reducing the appearance of wrinkles on the skin, (ii) treat inflammation, such as non-acne inflammation of skin, (iii) reducing the appearance of discoloration or puffiness around the eye, (iv) treat acne, (v) reducing the appearance of oil or pores on the skin, and/or (vi) darkening the skin.

In one embodiment, the present invention features a method of potentiating the activity of a cosmetically active agent by administering to skin in need of treatment with such active agent a composition comprising at least one compound of the formula I or formula II described below and such active agent.

In one embodiment, the present inventions features a composition comprising: (a) at least one compound of the formula I or formula II described below and (b) at least one member selected from the group consisting of a feverfew extract, a soy extract, an anti-inflammatory agent, retinol, a tocopherol, a sunscreen, a fungal extract, or an enzyme such as a protease.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

What is meant by "treat or treating a sign of aging on the skin" is reducing the appearance of wrinkles on the skin and/or enhancing the firmness or elasticity of the skin, including but not limited to, treating sagging, lax and loose skin or tightening skin.

What is meant by "potentiating the activity of a cosmetically active agent" is promoting, enhancing or sustaining the activity of other cosmetically active agents, such as anti-inflammatory active agents or retinoids, such as retinol and retinoic acid.

What is meant by "treating acne" is reducing or preventing acne or rosacea. In one embodiment, the composition used to treat acne does not contain retinoic acid, safflower oil (such as safflower oil containing linoleic acid), or linoleic acid.

What is meant by "treating inflammation of skin" is reducing or preventing redness or inflammation of skin. What is meant by "treating non-acne inflammation of skin" is reducing or preventing redness or inflammation of skin not caused by acne. In one embodiment, the composition used to treat inflammation does not contain retinoic acid, safflower oil, or linoleic acid.

What is meant by a "tocopherol" is alpha-tocopherol, or an isomer thereof (such as beta-tocopherol, delta-tocopherol or gamma-tocopherol), or a salt or ester thereof (such as an alpha-tocopherol acetate, succinate, or palmitate).

What is meant by a "sunscreen" is an active ingredient that absorbs, reflects, or scatters radiation in the U wavelength from 290 to 400 nm. Examples of sunscreens approved by the U.S. Food & Drug Administration include Avobenzone, Cinoxate, Dioxybenzone, Ensulizole, Homosalate, Menthyl anthranilate, Octocrylene, Octyl dimenthyl PABA, Octyl methoxycinnamate, Octyl salicylate, Oxybenzone, Sulisobenzone, Titanium dioxide, Trolamine salicylate, and Zinc oxide. Examples of additional sunscreens approved in the European Union include 3-Benzylidene camphor, Benzylidene camphor sulfonic acid, Bisymidazylate, Camphor benzalkonium methosulfate, Diethylamino hydroxybenzoyl hexyl benzoate, Diethythexyl butamido triazone, Dimethicodiethylbenzal malonate, Drometrizole trisiloxane, Ecamsule, Ensulizole, Isoamyl p-methoxycinnamate, 4-Methylbenzylidene camphor, PEG-25 PABA, Polyacrylamidomethyl benzylidene camphor, Tinosorb-M, and Tinosorb-S.

What is meant by an "anti-inflammatory agent" is an agent that has and IC50 of less than or equal to 100 µg/ml for Interleukin-2, Interferon-gamma, tissue necrosis factor-alpha, and/or granulocyte macrophage stimulating factor in the assay set forth below in Example 6. Examples of anti-inflammatory agents include, but are not limited to non-steroidal anti-inflammatory agents (e.g., ibuprofen, aspirin, naproxen, and acetaminophen), anesthetics (e.g., benzocaine, lidocaine, and pramoxine hydrochloride), corticosteroids (e.g., betamethasone dipropionate, betamethasone valerate, clobetasol propionate, diflorasone diacetate, halobetasol propionate, amcinonide, desoximetasone, fluocinonide, fluocinolone acetonide, halcinonide, triamcinolone acetate, hydrocortisone, hydrocortisone valerate, hydrocortisone butyrate, aclometasone dipropionte, flurandrenolide, mometasone furoate, methylprednisolone acetate), Vitamin D compounds (e.g. calcipotriene), and various plant extracts (e.g., feverfew and soybean extracts).

What is meant by a "product" is a product in finished packaged form. In one embodiment, the package is a container such as a plastic, metal or glass tube or jar containing the composition. The product may further contain additional packaging such as a plastic or cardboard box for storing such container. In one embodiment, the product contains instructions directing the user to administer the composition to (i) treat at least one sign of aging on the skin selected from the group consisting of enhancing the elasticity of said skin, enhancing the firmness of said skin, and reducing the appearance of wrinkles on the skin, (ii) treat non-acne inflammation of skin, and/or (iii) discoloration or puffiness around the eye. Such instructions may be printed on the container, label insert, or on any additional packaging.

What is meant by "contract a skin cell" is to reduce the length of at least one dimension of the skin cell. Examples of skin cells include, but are not limited to, keratinocytes.

What is meant by "promoting" is promoting, advertising, or marketing. Examples of promoting include, but are not limited to, written, visual, or verbal statements made on the product or in stores, magazines, newspaper, radio, television, internet, and the like.

For promoting the contraction of skin cells, examples of such statements include, but are not limited to, "contracts skin cells," "contracts keratinocytes," "shrinks skin cells," and "shrinks keratinocytes". Examples of such visual statements include digital images, pictures, drawings, or movies of skin cells depicting contracted cells and/or the contraction of cells (e.g., showing a reduction in the length of at least one dimension of the skin cell). In one embodiment, the skin cells are of the upper epidermis.

For promoting the treatment of signs of aging, examples of such statements include, but are not limited to, "enhances skin elasticity," "improving visible and tactilely perceptible manifestations of the skin," "increases skin elasticity or firmness," "restores skin elasticity," "treats sagging or lax skin," "reduces the appearance of cellulite," "lifts the skin," and "lifts the face," "firms the skin," "firms the face," "younger skin," "restores youthful firmness", "improves facial contours," and "makes skin look younger."

For promoting the treatment of inflammation, examples of such statements include, but are not limited to, "reduces inflammation," "reduces redness," and "reduces the appearance of inflammation."

For promoting the reduction in the appearance of discoloration or puffiness around the eye, examples of such statements include, but are not limited to, "reduces puffiness around the eyes," "reduces the appearances of bags under the eyes," "reduces the appearance of dark circles under the eyes," and "treats dark circles under the eyes."

For promoting the treatment of acne, examples of such statements include, but are not limited to, "treats acne," "prevents acne," "reduces acne lesions, comedones, or pimples," "reduces the appearance of acne lesions, comedones, or pimples," "reduces the appearance of acne breakouts and blemishes," "preventing, controlling or regulating the appearance of acne breakouts and blemishes", and "reduces breakouts and blemishes."

For promoting the reduction in the appearance of oil on the skin, examples of such statements include, but are not limited to, "reduces the appearance of sebum," "preventing, controlling or regulating the production of sebum," "reduces sebum," "reduces the appearance of oily/shiny skin," "reduces the appearance of greasy skin," and "reduces shine on the skin." In one embodiment, the composition is applied to skin not in need of treatment for acne (i.e., skin not suffering from acne).

For promoting the reduction in the appearance of pores on the skin, examples of such statements include, but are not limited to, "reduces the size of pores," "minimizes the appearance of pores," "refines the appearance of pores," "reduces the visibility or pores," and "closes pore opening." In one embodiment, the composition is applied to skin not in need of treatment for acne (i.e., skin not suffering from acne).

For promoting the darkening of skin, examples of such statements include, but are not limited to, "tans the skin," "darkens the tone of skin," and "reduces the appearance of light area of the skin", "enhances or promotes glow of skin," "enhances or promotes radiance of skin," "bronzes the skin,"

and "darkens the shade of skin." In one embodiment, the composition used to darken the skin does not contain dihydroxy acetone.

As used herein, the term "wrinkle" includes fine line, fine wrinkles, coarse wrinkles, cellulite, scars, and stretch marks. Examples of wrinkles include, but are not limited to, fine lines around the eyes (e.g., "crow's feet"), forehead and cheek wrinkles, frown-lines, and laugh-lines around the mouth.

As used herein, "administering to skin in need of such treatment" means contacting (e.g., by use of the hands or an applicator such, but not limited to, a wipe, tube, roller, spray, or patch) the area of skin in need such treatment or an area of skin proximate to the area of skin in need of such treatment (e.g., to contract an area of skin proximate to the area of need of treatment, thereby tightening the area of skin in need of such treatment).

As used herein, "composition" means a composition suitable for administration to the skin.

As used herein, "cosmetically-acceptable" means that the ingredients which the term describes are suitable for use in contact with the skin without undue toxicity, incompatibility, instability, irritation, allergic response, and the like.

As used herein, "safe and effective amount" means an amount of the compound, carrier, or of the composition sufficient to induce an enhancement in tissue elasticity, but low enough to avoid serious side effects. The safe and effective amount of the compounds or composition will vary with the area being treated, the age, health and skin type of the end user, the duration and nature of the treatment, the specific compound or composition employed, the particular cosmetically-acceptable carrier utilized, and like factors.

Compounds

The compositions of the present invention contain at least one compound of the formula I or formula II:

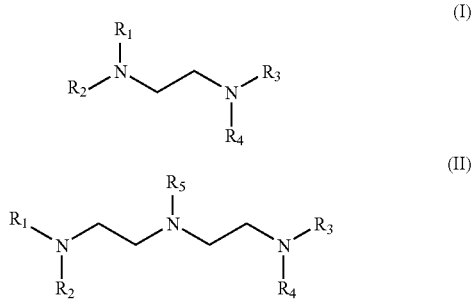

wherein R1, R2, R3, R4, and R5 independently, are selected from the group consisting of hydrogen, $C_1$-$C_6$ alkyl, and $C_1$-$C_6$ hydroxyalkyl; or a cosmetically-acceptable salt thereof.

In one embodiment, the compositions of the present invention contain at least one compound of the formula I and R1, R2, R3, and R4 are selected from the group consisting of $C_1$-$C_3$ alkyl and $C_1$-$C_3$ alkanol. In a further embodiment, at least one of R1, R2, R3, and R4 of formula I is a $C_2$-$C_3$ alkanol group bearing at least one hydroxyl group.

Examples of compounds of formula I include, but are not limited to, N,N,N',N'-Tetrakis(2-hydroxypropyl)ethylenediamine (THPED), N, N, N', N'-Tetrakis(2-hydroxyethyl)ethylene diamine (THEED), N, N, N', N'-tetramethylethylene diamine (TEMED) (the structures of which are set forth below), enantiomers thereof, or diastereoisomers thereof, or cosmetically-acceptable salts thereof.

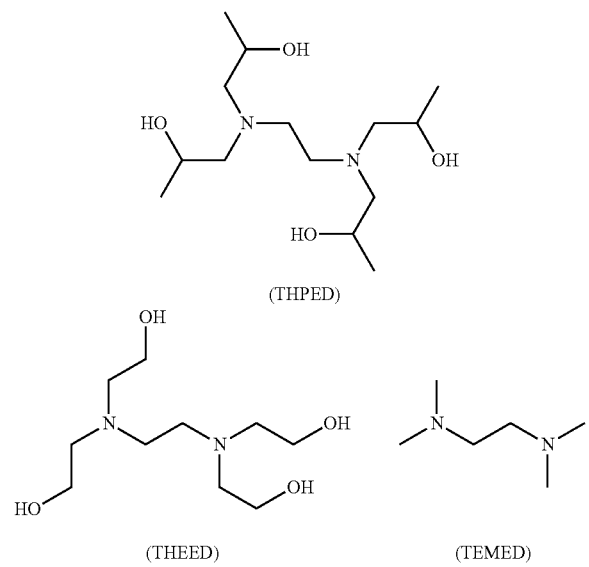

The synthesis of N,N,N',N'-tetrakis(2-hydroxypropyl) ethylenediamine from the reaction of ethylenediamine with of propylene oxide is described in U.S. Pat. No. 2,697,118.

The compounds of the present invention may also be present in the form of cosmetically acceptable salts. For use in medicine, the salts of the compounds of this invention refer to non-toxic "cosmetically acceptable salts," cosmetically acceptable acidic/anionic or basic/cationic salts. Cosmetically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Cosmetically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

In one embodiment, the compositions of present invention contain from about 0.01% to about 10% by weight of such compound, such as from about 0.1% to about 5% by weight of such compound, such as from about 0.5% to about 3% by weight of such compound. In one embodiment, the composition contains at least 1% by weight of such compound, such as at least about 2% by weight of such compound.

Compositions

The compositions useful in the present invention involve formulations suitable for administering to the target tissues, such as mammalian skin such as human skin. In one embodiment, the composition contains a safe and effective amount of (i) compounds of the present invention and (ii) a cosmetically-acceptable carrier. In one embodiment, the cosmetically-acceptable carrier is from about 50% to about 99.99%, by weight, of the composition (e.g., from about 80% to about 99%, by weight, of the composition).

The compositions may be made into a wide variety of product types that include but are not limited to solutions, suspensions, lotions, creams, gels, sticks, sprays, ointments, cleansing liquid washes and solid bars, shampoos and hair conditioners, pastes, foams, powders, mousses, shaving creams, wipes, patches, nail lacquers, wound dressing and adhesive bandages, hydrogels, film-forming products, facial and skin masks, make-up such as foundations, mascaras, eye lines, eye shadows, and lipsticks, and the like. These product types may contain several types of cosmetically-acceptable carriers including, but not limited to solutions, suspensions, emulsions such as microemulsions and nanoemulsions, gels, solids and liposomes. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, and mixtures thereof.

A lotion can be made from such a solution. Lotions typically contain from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook").

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus.from about 0.1% to about 2% of a thickening agent(s). Examples of thickening agents include, but are not limited to, those set forth in the ICI Handbook pp. 1693-1697.

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp.1673-1686.

Lotions and-creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, and wipe containing powder).

The compositions useful in the subject invention may contain, in addition to the aforementioned components, a wide variety of additional oil-soluble materials and/or water-soluble materials conventionally used in compositions for use on skin at their art-established levels.

Additional Cosmetically Active Agents

In one embodiment, the composition further contains another cosmetically active agent in addition to the above compounds. What is meant by a "cosmetically active agent" is a compound (e.g., a synthetic compound or a compound isolated from a natural source, or a natural extract containing a mixture of compounds) that has a cosmetic or therapeutic effect on the tissue, including, but not limiting to, lightening agents, darkening agents such as self-tanning agents, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, anti-callous agents, agents for skin conditioning, anti-cellulite agents, fluorides, and odor-control agents such as odor masking or pH-changing agents.

In one embodiment, the cosmetically active agent is selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids and retinoid precursors such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as aloe vera, Feverfew, and Soy, and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, and vitamin B12, vitamin C, vitamin K, vitamin E such as alpha, gamma or delta-tocopherol, and derivatives (such as salts and esters) and mixtures thereof.

Examples of hydroxy acids include, but are not limited, to glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention, include, but not limited to, extracts containing flavonoids, isoflavonoids, and their derivatives such as genistein and diadzein (e.g., such as Soy and Clover extracts, extracts containing resveratrol and the like. Examples of such natural extracts include grape seed, green tea, pine bark, and propolis.

Examples of enzymes include, but are not limited to, proteases such as fungal proteases, bacterial proteases or mammalian proteases. Examples of such proteases include, but are not limited to, pepsin, cathepsin, human urinary acid protease, fungal proteases derived from *Neurospora oryzae, Mucor pusillus, Mucor miehei, Rhizopus chinensis*, or *Endothia parasitica*, and bacterial proteases rhizopuspepsin, penicillopepsin, and endothiapepsin. Further, the proteases may be derived from processes involving genetic engineering processes and techniques.

Examples of fungal extracts include, but are not limited to, extracts from *Neurospora oryzae, Mucor pusillus, Mucor miehei, Rhizopus chinensis*, or *Endothia parasitica Mucor Miehei*. Examples of compositions containing such proteases and fungal extracts are disclosed in U.S. Pat. No. 5,976,556.

The irritation mitigation effects of the compounds of formula I and II can help mitigate the skin irritation effects of certain irritating cosmetically active agents. Examples of such skin-irritating cosmetically active agents include, but not limiting to, retinoid and its derivatives, benzoyl peroxide, retinoids, and alpha-hydroxy acids. Examples of retinoid include, but are not limited to, retinol, retinoic acid, retinyl palmitate, retinyl acetate, retinal, and retinyl propionate. Examples of alpha-hydroxy acids include, but are not limited to, lactic acid and glycolic acid.

In one embodiment, the composition further contains a compound selected from the group consisting of caffeine, vitamin A, vitamin E, vitamin K, vitamin C, and salt and esters thereof or an extract selected from the group consisting green tea extract, horsechestnut extract, live yeast cell extract, and cucumber extract In one embodiment, the composition further contains a self-tanning agent such as dihydroxy acetone, forskolin, erthulose, skin darkening peptides such as LIGR, SLIGRL, and others disclosed in US Patent Applications 2002/0197219, 2002/0197281, 2003/0138388, and 2003/0232743, melanin and melanin derivatives (e.g, both melanin polymers and lower molecular weight water-soluble melanin derivatives), and extracts of the plant genus Hedychium, Rhubarb, Bearberry, and Onosis such as Onosis Spinosa root extract. Examples of synthetic melanin derivatives are disclosed in U.S. Pat. Nos. 5,618,519, 5,384,116, and 5,227,459 and U.S. Patent Application No. 2005/0129633. Examples of soluble melanin derivatives are disclosed in U.S. Pat. Nos. 5,744,125, 5,225,435, 5,218,079, and 5,216,116. Examples of commercially available soluble melanin derivatives include Melasyn-100® from San-mar laboratories, Inc. (Elmsford, N.Y.) and MelanZe® from Zylepsis (Ashford, Kent, United Kingdom).

In one embodiment, the composition further contains a retinoid, and alpha-hydroxy acid, a soy extract, a phytoestrogen, an estrogen, an astringent such as witch hazel, triclosan, cerulenin, alpha-methylene-gamma-butyralactone, glycine derivatives such as capryloylglycine and methylglycine, salicylic acid, or benzoyl peroxide.

Plant Extract

In one embodiment, the compositions of present invention further contain a plant extract. What is meant by a "plant extract" is a blend of compounds isolated from a plant. Such compounds may be isolated from one or more part of the plant (e.g., the whole plant, flower, seed, root, rhizome, stem, fruit and/or leaf of the plant) by physically removing a piece of such plant, such as grinding a flower of the plant. Such compounds may also be isolated from the plant by using extraction procedures well known in the art (e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide).

In one embodiment, the plant extract (e.g., a feverfew extract or a soybean extract) is present in the composition in an amount from about 0.001% to about 20% by weight, in particular in an amount from about 0.1% to about 10% by weight of the composition. Unless stated otherwise, the weight of the extract refers to the dry weight of the extract.

Feverfew Extract

In one embodiment, the compositions of present invention further contain a feverfew extract. What is meant by a "feverfew extract" is a blend of compounds isolated from a feverfew plant. Examples of such compounds, include, but are not limited to, apigenin-7-glucoside, apigenin-7-glucuronide, 1-β-hydroxyarbusculin, 6-hydroxykaempferol-3,7-4'-trimethylether (Tanetin), 6-hydroxykaempferol-3,7-dimethyl ether, 8-β-reynosin, 10-epicanin, ascorbic acid, beta-carotene, calcium, chromium, chrysanthemolide, chrysanthemomin, chrysarten-A, chrsyarten-c, chrysoeriol-7-glucuronide, cobalt, cosmosiin, epoxyartemorin, luteolin-7-glucoside, luteolin-7-glucuronide, mangnoliolide, parthenolide, quercetagentin-3,7,3'-trimethylether, quercetagetin-3'7-dimethylether, reynosin, tanaparthin, tanaparthin-1α,4α-epoxide, tanaparthin-1β,4β-epoxide, β-costunolide, 3-β-hydroxy-parthenolide, and 3,7,3'-trimethoxyquercetagetin. The α-unsaturated γ-lactones present in the feverfew plant, such as parthenolide, are known to cause the allergic reactions. Therefore, in one embodiment, the feverfew extract is substantially free of the allergy causing α-unsaturated γ-lactones. The preparation of feverfew extract that is substantially free of parthenolide is disclosed in Example 1 in U.S. Patent Application No. 20040105905.

Soybean Extract

In one embodiment, the compositions of present invention further contain a soybean extract. What is meant by a "soybean extract" is a blend of compounds isolated from soybean.

The soybean extract may contain only a portion of the soybean (e.g., an extract of the soybean such as a lipid reduced soybean powder or filtered soymilk) or may contain the entire soybean (e.g., a ground powder of the soybean). The soybean extract may be in the form of a fluid (e.g., soymilk) or a solid (e.g., a soybean powder or soymilk powder).

The soybean extract may be soybean powder. Soybean powder may be made by grinding dry soybeans. The soybean powder may be lyophilized. Soymilk and soymilk powder are also useful soybean extracts. Soymilk is a combination of solids derived from soybeans and water, the mixture of which has some or all of the insoluble constituents filtered off. Soymilk powder is evaporated soymilk, which in one embodiment, is in a lyophilized or spray-dried form. Procedures for manufacturing soymilk include, but are not limited to, the following three procedures. First, soymilk may be made by placing soybeans into water to allow them to absorb the water. The swelled beans are then ground and additional water is then added. The mixture may then be filtered to remove any insoluble residue. Second, soymilk may also be prepared from soybean powder. Soybean powder is thoroughly mixed with water (e.g., for at least one hour), which may then be followed by a filtration process to remove insoluble residues. Third, soymilk can also be reconstituted from soymilk powder by adding water. The soymilk may comprise from about 1% to about 50%, by weight. (e.g., from about 5% to about 20%, by weight) of solids from the soybean.

The known active ingredients of soybeans include, but not limiting to, isoflavones, phytoestrogens, genistein, daidzein, glycitein, saponins, and phytosterols. The soybean extracts useful in this invention may be produced from all soybean species, regardless of their geographic origin, sun exposure, harvest time and the like. However, specific strains, geographic origins or growth conditions might be preferred. For example, but not limiting to, soybean strains particularly rich in its Soybean Trypsin Inhibitor (STI) content or in isoflavone content, or growth conditions that result in STI or isoflavone enrichment in the bean, might be preferred.

In one embodiment, the soybean extract is a non-denatured soybean extract. "Denaturation" is defined in the Bantam Medical Dictionary (1990 edition) as "the change in the physical and the physiological properties of a protein, that are brought about by heat, X-rays or chemicals. These changes include loss of activity (in the case of enzymes) and loss (or alteration) of antigenicity (in the case of antigens)". What is meant by "non-denatured plant extract" is a product extracted or derived from a plant in which the processing for the derivation of such plant extract (e.g., the temperature, extraction media) did not eliminate its protease inhibitory activity. One such protease is trypsin. In one embodiment, the non-denatured state of the soybean extract of this invention is measured by the presence of an intact soybean trypsin inhibitor (STI) protein, or by its trypsin inhibitory activity.

It should be noted that the soybean extracts useful in the compositions of this invention may have a distinctive odor. If necessary, the odor of the extracts may be reduced by using soybean products derived from specific strains of soybeans known to produce reduced-odor, including, but not limited to, lipoxygenase-2-deficient beans and those having modified sugar profile, and the like. A process to reduce oxygen levels in the formulation may also reduce the odor. Various masking agents or fragrances may also be used to mask the odor. One way to make soymilk is to soak the soybeans in deionized or purified water for several hours, and grind them after they were fully hydrated, with the addition of small quantities of water. The grinding process allows the soybean milk to be extracted. After collection, the soybean milk may be filtered to remove any residual parts of the bean husk.

The soymilk used in the formulations described below can be fresh soymilk as described above, or may be made from soybean powder and water. The soybean powder is milled from soybeans and may also be lyophilized, spray dried, or freeze-dried and the resulting soymilk may or may not be filtered. Such prepared soymilk may have from about 1 to about 90% by weight dry soybean powder. Another example is the use of soymilk powder, made from lyophilized, spray dried or freeze-dried soymilk, with the addition of water and finished with or without filtration or homogenization. Other methods of soybean extraction could also be used to create the active ingredients in the formulations described below. For example, the active ingredients could be extracted from ground soybeans using ethanol/water mixtures, followed by the removal of the ethanol from the extract, in such ways that the serine protease inhibitory activity of the soybean will be retained, and preferably that the protein STI will remain intact. In one embodiment, the soybean extracts utilized in the present invention have a microbial content of less than about 1,000 cfu per gram (such as less than about 100 cfu per gram) of the soybean extract.

The soybean extract may be exposed to gamma irradiation. The soybean extract may be exposed to from about 2 to about 30 kGy of gamma irradiation, such as from about 5 and about 10 kGy of gamma irradiation. Such treatment reduces the microbial content of the soybean extract, while maintaining its biological activity (e.g., serine protease inhibitory activity). The treatment of soybean extracts with gamma irradiation maintains the cosmetic elegance of the composition, such as maintained natural colors and does not induce significant malodors.

Other anti-microbial processes that also maintain the protease inhibitory activity of the soybean extract that can be practiced alone or in combination with gamma irradiation, include, but are not limited to, exposure to x-rays, high energy electron or proton beams, ultraviolet radiation, hydrostatic pressure, and addition of chemical agents possessing antimicrobial activity, and combinations thereof.

Other Materials

Various other materials may also be present in the compositions useful in the subject invention. These include humectants, proteins and polypeptides, preservatives and an alkaline agent. Examples of such agents are disclosed in the ICI Handbook, pp. 1650-1667. The compositions of the present invention may also contain chelating agents (e.g., EDTA) and preservatives (e.g., parabens). Examples of suitable preservatives and chelating agents are listed in pp. 1626 and 1654-55 of the ICI Handbook. In addition, the compositions useful herein can contain conventional cosmetic adjuvants, such as colorants such as dyes and pigments, opacifiers (e.g., titanium dioxide), and fragrances.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

Use

The composition according to the invention can be used to treat a variety of skin conditions, such as the signs of aging, discoloration and puffiness around the eye, acne, light areas of the skin, visible pores and oil on the skin, dry skin, and a variety of non-acne inflammatory disorders such as those caused by both external and inherent conditions. Examples of such inflammatory disorders which may be treated by topical use of the compositions of this invention include, but are not limited to the following: arthritis, contact dermatitis, atopic dermatitis, psoriasis, seborrheic dermatitis, eczema, allergic dermatitis, polymorphous light eruptions, inflammatory dermatoses, folliculitis, alopecia, poison ivy, insect bites, irritation induced by extrinsic factors including, but not limited to, chemicals, trauma, pollutants (such as cigarette smoke) and sun or wind exposure, and secondary conditions resulting from inflammation including but not limited to xerosis, hyperkeratosis, pruritus, post-inflammatory hyperpigmentation, scarring and the like. Examples of such discoloration and puffiness around the eye include, but are not limited to, dark circles and bags under the eye. In one embodiment, the dark circles under the eye being treated are a result of the increase concentration of blood in the skin under the eye.

The composition and formulations containing such compositions of the present invention may be prepared using methodology that is well known by an artisan of ordinary skill.

EXAMPLE 1

Electric Cell-Substrate Impedance Detection

Electrical changes due to the presence of a cell layer can be used to calculate cell morphological parameters including the barrier function of the cell layer (the spacing between the ventral side of the cell and the substratum) and the cell membrane capacitance (Giaever and Keese, Proceedings of National Academy of Sciences 88, 7896, 1991).

Current flowing between a reference electrode, onto which cells or cell cultures may be attached, and a larger counter electrode using normal culture medium as the electrolyte can be used to detect changes in cell morphological parameters. In the absence of cells on the electrode, the current flows unrestrained from the surface of the electrodes. In the presence of cells attached and spread upon the electrode, the current must now flow in the spaces under and between the cells, as the cell membrane act as insulators.

The electrical changes of living, viable cells can be sampled rapidly, in real time, over an extended period of time, and the measurements are the measurement is non-invasive. An example of this technology is the Electric Cell-substrate Impedance Sensing System (ECIS) available from Applied Biophysics (Troy, N.Y.). Electrical changes in keratinocyte morphological parameters can be used to identify novel compounds for anti-aging benefits.

Human keratinocytes and Epilife culture media (Cascade Biologics, Portland, Oreg.) were cultured at 37° C. in a humidified atmospheres of 5% $CO_2$/95% air. Electric Cell-substrate Impedance Sensing System (ECIS) electrode arrays (Applied Biophysics, Troy, N.Y.) were coated with 0.01 mg/ml Laminin V (Sigma Aldrich, St Louis, Mo.) in sterile Phosphate Buffered Saline (Gibco Life Sciences, San Diego, Calif.). Human keratinocytes were prepared at a density of $0.125 \times 10^6$ cells/mL in Epilife culture media. Human keratinocytes were plated at $5.0 \times 10^4$ cells/electrode well and cultured at 37° C. in a humidified atmospheres of 5% $CO_2$/95% $O_2$ for 24-48 hrs. Capacitance changes (in nanofarads, nF) of keratinocytes were measured using a Electric Cell-substrate Impedance Sensing System (ECIS) Model 1600R (Applied Biophysics, Troy, N.Y.) using the method of Wegener and co-workers (Wegener J, Keese C R, Giaever I, Exp Cell Res. 259:158-166, 2000) at a frequency of 40,000 Hz. Capacitance readings are inversely related to the contact area of a cell onto the ECIS electrode array, the greater the cell area contacting the electrode the smaller the capacitance readings (Wegener J, Keese C R, Giaever I, Exp Cell Res. 259:158-166, 2000). Conversely as a cell contracts or shrinks, the contact area of the cell onto the ECIS electrode array decreases, resulting in an increase in the capacitance readings. The change in capacitance readings for each treatment groups was integrated over 5 hrs as a function of area-under-the-curve (AUC) analysis from approximately 1000 keratinocyte cells. These calculations are based on the trapezoid theorem. The AUC of the media curve was subtracted from the compound treated group. A positive AUC difference indicates keratinocyte contraction, the greater the AUC difference the greater the amount of keratinocyte contraction. The following compounds were used in the example: N,N,N',N'-Tetrakis(2-hydroxypropyl)ethylenediamine (THPED, available from BASF under the tradename "Quadrol" or "Neutrol") and 2-(dimethylamino)ethanol (available from BASF under the tradename "DMAE"). DMAE is a known skin-firming agent. The compounds were diluted into Hank's Buffered Salt Solution (HBSS; Gibco Life Sciences, San Diego, Calif.) and the pH of the solution adjusted to between pH 7.2-7.3. The pH of the HBSS without compounds ("Media Alone") was also adjusted to pH 7.2-7.3.

Based on this example, it can be seen from the results on table I, that DMAE and THPED induces a dose-dependent contraction or shrinkage of keratinocyte cell area compared to media treatment alone as measured by keratinocyte capacitance.

TABLE I

Quantization of Electrical Capacitance Contraction of Human Keratinocytes (Mean ± Std Dev)

| Treatment | Concentration (% V/V) | | | |
|---|---|---|---|---|
|  | 0% | 0.01% | 0.05% | 0.1% |
| Media Alone | 15.8 ± .8 |  |  |  |
| Media + THPED |  | 29.2 ± 3.2** | 35.1 ± 5.3* | 44.5 ± 9.1* |
| Media + DMAE |  | 22.82 ± 4.1** | 28.8 ± 5.6** | 36.1 ± 5.9* |

*= $P < 0.05$ compared to AUC for Media Alone treated group using a paired t-Test.
**= $P < 0.1$ compared to AUC for Media Alone treated group using a paired t-Test

EXAMPLE 2

Contraction of Human Keratinocytes with THPED Using Real Time Visual Microscopy

Human keratinocytes and Epilife culture media (Cascade Biologics, Portland, Oreg.) were cultured at 37° C. in a humidified atmospheres of 5% $CO_2$/95% air. Glass Cover Slides (Applied Biophysics, Troy, N.Y.) were coated with 0.01 mg/ml Laminin V (Sigma Aldirch, St Louis, Mo.) in sterile Phosphate Buffered Saline (Gibco Life Sciences, San Diego, Calif.). Human keratinocytes were prepared at a density of $0.125 \times 10^6$ cells/mL in Epilife culture media. Human keratinocytes were plated at $3.75 \times 10^4$ cells/well on a 6 well plate containing Laminin coated coverslips and cultured at 37° C. in a humidified atmospheres of 5% $CO_2$/95% $O_2$ for 48 hrs. Individual coverslips were transferred to a open bath imaging chamber (Warner Instruments, Hamden, Conn.) mounted on a Leica inverted microscope (Leitz DM1L) with an attached CCD camera. Cells were perfused with Hank's Buffered Salt Solution (HBSS; Gibco Life Sciences, San Diego, Calif.) at flow rate of 1 ml/min using a peristaltic pump (Cole Parmer, Vernon Hills, Ill.). DMAE or THPED was diluted into Hank's Buffered Salt Solution and the pH of the solution adjusted to between pH 7.2-7.3. The pH of the HBSS without DMAE or THPED ("Media Alone") was also adjusted to pH 7.2-7.3. Human keratinocytes were perfused for 10 minutes with buffer alone to establish basal conditions at which time, buffer containing various concentrations of DMAE or THPED were perfused onto keratinocytes. Images were collected of a field of keratinocytes containing 10-20 cells at 0, 10 and 20 minutes of treatment using ImagePro software. Cell area was determined using Scion Image software (Version 4.0.2), and reductions in cell area were reported as the ratio of cell area after treatment to cell area prior to treatment Based on this example, it was found (as shown in Table II) that DMAE and THPED induces a dose-dependent contraction or shrinkage of keratinocyte cell area as determined by keratinocyte surface area.

TABLE II

Quantization of Visual Contraction of Human Keratinocytes with THPED and DMAE (Mean ± Std Dev) Concentration (% V/V)

| Treatment | 2 Min | 10 Min | 20 Min |
|---|---|---|---|
| Media Alone | | | 2.1% ± 3.2% |
| Media + DMAE (0.01%) | | 4.82% ± 0.68%* | 6.22% ± 0.95%* |
| Media + DMAE (0.05%) | | 16.40% ± 2.58%* | 18.04% ± 3.09%* |
| Media + DMAE (0.1%) | | 23.61% ± 3.03%* | 33.83% ± 2.96%* |
| Media + THPED (0.1%) | 32.9% ± 11.3%* | 37.9% ± 10.7%* | 47.3% ± 12.7%* |

*= $P < 0.05$ compared to cell area of keratinocytes prior to treatment with THPED using a paired t-Test.

Based on this example, it can be seen that DMAE and THPED are able to significantly induce a rapid contraction or shrinkage of keratinocyte cell area.

EXAMPLE 3

Reviscometer® RVM 600 Reading in the Upper Inner Arm

The Reviscometer® RVM 600 (Courage and Khazaka, Cologne, Germany) measures the propagation time of an elastic shear pulse in viscoelastic materials. As the preferred disposition of the collagen fibers corresponds to the skin's cleavage line (Lange's lines), the speed of propagation of elastic disturbances on the skin will depend strongly on its orientation. Skin sites on the body where the skin is the loosest would present the strongest orientation effects, e.g. on the upper inner arm, the neck, the thighs and the abdomen based on collagen fiber orientation.

In this study we chose an instrument that allows the determination of directional tension along the surface of the skin. The velocity of sound depends on the density and tension of the material through which it is propagating, for example sound travels faster in water than it does in air and faster yet in a solid. Mechanical vibrations propagate faster the higher the tension, like a guitar string the higher the tension the higher the frequency of oscillation after plucking. The probe that comes in contact with the skin of the instrument in question is composed of two transducers placed 1.5-2 mm apart and mounted on two independent supports. Then one transducer generates a motion of small amplitude (<1 mm) and the second transducer determines when the disturbance generated by the first transducer arrives at its location. From this time, we can calculate the velocity of propagation and, therefore, the tension along the skin. In the limit where the motion of the transducer is less than 100 microns, the instrument would probably probe the tension in the epidermis and as the motion becomes larger the motion would include the dermis. The instrument used in this study generates a motion that probes the epidermis and the superficial dermis. The time that it takes the acoustic pulse to go from transmitter to receiver is the measured parameter called Resonance Running Time (RRT). The RRT depends on the directional orientation of the collagen bundles. Readings must be performed in different angles: 0°, 45°, 90° and 135°. In this study readings as function of the angle were taken in increments of 3°; covering an angular field of 100° range. The anisotropy (A) of the measured parameter, $RRT_{max}/RRT_{min}$, and the full width at half maximum (FWHM) obtained from a Gaussian fit of the RRT as a function of the measured angle are two new mechanical parameter that change with age. Its ratio A/FWHM is a new mechanical parameter that we can use to predict the subjects age since we obtained a p value of <0.001 for this ratio as a function of age. In this study we will express the skin firming as a ratio of the Anisotropy before and after product application.

Skin viscoelastical measurements were performed as a function the direction with a Reviscometer® (Model RVM 600, Courage Khazaka, Cologne, Germany). The probe is held perpendicular to the skin surface by a hollow cylindrical holder that is attached to the surface of the skin with double stick tape (positioning top). The holder has marks along its periphery at angular intervals of 45°. In our instrument we modified the probe-holder assembly by placing a mm scale on the probe and another on the holder. Then we carried out measurements by rotating the probe within the holder so that the mm lines of the scale would align with each other, this corresponded to making measurements every 3° for a total interval of 100°.

The skin viscoelastical measurements were taken on the upper inner arm of 30 subject. Two sites were chosen in each arm, readings were taken as described above before and 45 minutes after product application. In one of the sites was applied a placebo formulation (no THPED) and in the second site a formulation containing 2.5% of THPED (as described in Example 4), was applied. After the gaussian fit, the Anisotropy ratio, before and after product application, was calculated.

It was found that the THPED formulation decreases the skin anisotropy 3 fold, as compared to 1.5 fold for the placebo formulation. Using a Minitab® software for the statistical analysis comparing THPED formulation against placebo, we obtained a p<0.001. This shows that THPED treated sites can tight and firm the skin and this effect is statistically significant.

Compositions containing DMAE were also tested in the same methodology as described above. The upper inner arms of subjects were treated with products that contained either 0% DMAE (placebo), 0.5% DMAE, 1% DMAE, 2% DMAE, or 3% DMAE. The anisotropy was measured both before and 35 minutes after product application. The anisotropy ratio shows a dose response for DMAE indicating that the contraction of the keratinocytes, as seen in the Confocal Microscopy example (example 3), can firm and tight the skin as well deliver anti-aging benefits to the skin. Table V shows the firming effect (anisotropy ratio) for the DMAE as a function of DMAE concentration in percentage.

TABLE V

| DMAE Concentration (%) | Firming ($A_{before}/A_{after}$) |
|---|---|
| Placebo | 1.1 ± 1.1 |
| 0.5 | 6.5 ± 5.8 |
| 1 | 9.5 ± 6.3 |
| 2 | 14.5 ± 4.8 |
| 3 | 20.9 ± 5.0 |

EXAMPLE 4

Topical Composition

The following is a description of the manufacture of a topical lotion composition containing THPED. Into a primary glass beaker, 545.60 g of deionized water was weighed and heated to 78-80° C. While mixing at moderate speed, 15.0 g of PVM/MA Decadiene Crosspolymer available from International Specialty Products (Wayne, N.J.) under the tradename "Stabileze QM" was added and mixed until homogenous at 78-80° C. The beaker was removed from heat, and 1.0 g of Disodium EDTA available from Dow Chemical (Midland, Mich.) under the tradename "Versene NA", 7.5 g of Sucrose Cocoate available from Croda (Edison, N.J.) under the tradename "Crodesta SL-40", 7.5 g of PEG-6 Capric/Caprylic Glycerides available from Croda under the tradename "Glycerox 767," and 10.0 g of Hexylene Glycol available from Pfaltz & Bauer Chemicals (Waterbury, Conn.) under the tradename "Hexylene Glycol" were added and mixed until uniform.

In a secondary beaker, 305.0 g of deionized water were weighed into a glass beaker. 25.0 g of N,N,N',N'-Tetrakis(2-hydroxypropyl)ethylenediamine available from BASF under the tradename "Quadrol" or "Neutrol" was added and mixed until uniform. When the temperature of the primary beaker was cooled to 40° C. or below, the contents of the second beaker were added to the primary beaker and mixed until uniform.

A buffering solution was prepared in a tertiary beaker by first weighing 12.4 g of deionized water into a glass beaker. 8.0 g of Anhydrous Citric Acid "Citric Acid," and 23.0 g of Glycolic Acid (70%) available from DuPont Chemical under the tradename "Glypure" were then added and mixed until uniform. The pH of the mixture in the primary beaker was adjusted to between 7.0-7.5 with Glycolic/Citric/Water mixture added from the tertiary beaker.

Then, 5.0 g of Talc available from Luzenac (Denver, Colo.) under the tradename "Windsor Talc 66" was added to the primary beaker and mixed-until uniform. 10.0 g of Nylon 12 available from Kobo Products, Inc (South Plainfield, N.J.) under the tradename "SP-10" was added to the primary beaker and mixed until uniform. 10.0 g of Silicone Quaternium-13 available from Biosil Technologies, Inc. (Paterson, N.J.) under the tradename "Biosil Basics SPQ" was added to the primary beaker and mixed until uniform. 10.0 g of Parabens available from Nipa Laboratories, Inc. (Wilmington, Del.) under the tradename "Phenonip" was added to the primary beaker and mixed until uniform. Finally, the mixture was homogenized for 5 minutes and cooled to 25° C.

EXAMPLE 5

Topical Composition

A topical formulation of Table VI was manufactured as follows. Into a primary glass beaker, deionized water, glycerin, hydroxycellulose, and parabens were added. N,N,N',N'-Tetrakis(2-hydroxypropyl)ethylenediamine (available from BASF under the tradename "Quadrol" or "Neutrol") was then added to the primary glass beaker, mixed until uniform and the pH of the mixture was adjusted to between 7.0-7.5 with Glycolic Acid. Following adjustment of the pH, Chrysantemum Parthenium Extract (Feverfew Powder Extract) was added and mixed until uniform.

Into a secondary glass beaker, Petrolatum, Distearyldimonium Chloride, Cetearyl Alcohol, Isopropyl Palmitate, and Dimethicone were added. The mixture in the secondary glass beaker was heated to 80° C., and mixed until uniform. When the temperature of the secondary beaker was cooled to 40° C. or below, the contents of the second beaker were added to the primary beaker along with Benzyl Alcohol and mixed until uniform. Finally, the mixture was homogenized for 5 minutes and cooled to 25° C.

TABLE VI

| Trade Name | INCI Name | % W/W |
|---|---|---|
| Deionized Water | Deionized Water | 63.68 |
| Glycerine 917 | Glycerin | 12 |
| Varisoft TA-100 | Distearyldimonium Chloride | 5 |
| Snow White Petrolatum U.S.P. | Petrolatum | 4 |
| Procol CS-20-D | Cetearyl Alcohol and Ceteareth-20 | 3 |
| Propal NF | Isopropyl Palmitate | 3 |
| Crodacol C-95 | Cetyl Alcohol | 2.5 |
| Quadrol | Tetrahydroxypropl Ethylenediamine | 2.5 |
| Glypure 70% | Glycolic Acid | 1.4 |
| Dow Corning 225 | Dimethicone | 1.25 |
| Benzyl Alcohol | Benzyl Alcohol | 0.6 |
| Feverfew Powder Extract | Chrysantemum Parthenium (Feverfew) Extract | 0.5 |
| Nipastat | Methylparaben and Butylparaben and Ethylparaben and Propylparaben | 0.3 |
| Natrosol 250 HHR | Hydroxyethylcellulose | 0.27 |

EXAMPLE 6

Immunomodulation of Human Peripheral Blood Lymphocyte Cytokine Release Stimulated with PHA The ability of various amines to affect the inflammatory responses was illustrated by its ability to reduce the production of cytokines by human lymphocytes stimulated with the T-cell receptor (TCR) activating agent phytohaemagglutinin (PHA) in the following assay.

Human leukocytes were collected from a healthy adult male via leukopheresis, and adjusted to a density Of $1 \times 10^6$ cells/mL in serum free lymphocyte growth medium (ExVivo-15, Biowhittaker, Walkersville, Md.). PBLs were stimulated with 10 µg/mL PHA in the presence or absence of test samples following published methods (Hamamoto Y., et al. Exp Dermatol 2:231-235, 1993). The following compounds were evaluated N,N,N',N'-Tetrakis(2-hydroxypropyl)ethylenediamine (THPED, available from BASF under the tradename "Quadrol" or "Neutrol"), N,N,N,N-Tetramethylethylenediamine (TEMED, available from Pfaltz & Bauer Chemicals (Waterbury, Conn.)), and Diethylenetriamine (available from Sigma-Aldrich) Following a 48 hour incubation at 37° C. with 5% $CO_2$, the supernatant was removed and evaluated for cytokine content using commercially available multiplex cytokine detection kit. The results are depicted on Table VII.

TABLE VII

| Compound | Dose | TNF % inh. | IL-2 % inh. | IFN % inh. | GMCSF % inh. |
|---|---|---|---|---|---|
| N,N,N,N- Tetramethylethylenediamine (TEMED) | 100 μg/ml | 41.8% | 42.9% | 58.6% | 53.1% |
| | 10 μg/ml | 33.6% | 6.6% | 36.9% | 47.4% |
| Tetrahydroxyethylethylenediamine (THEED) | 100 μg/ml | 44.5% | 61.8% | 49.5% | 23.0% |
| | 10 μg/ml | 35.8% | 27.7% | 23.7% | 16.6% |
| N,N,N',N'- Tetrakis(2- hydroxypropyl) ethylenediamine | 100 μg/ml | 46.1% | 41.3% | 37.9% | 15.8% |
| | 10 μg/ml | 13.3% | 10.6% | 18.1% | 10.3% |
| Diethylenetriamine | 100 μg/ml | 3.3% | −19.5% | −35.0% | 51.7% |
| | 10 μg/ml | 9.9% | 4.7% | −1.2% | 36.6% |
| Tris[2- (isopropylamino) ethyl] amine | 100 μg/ml | −15.3% | 2.3% | 12.5% | −52.8% |
| | 10 μg/ml | −10.7% | −7.7% | 20.3% | −26.4% |

(where IL = Interleukin-2 (Cytokine); IFN = interferon-gamma; TNF = tissue necrosis factor-alpha; GM-CSF = granulocyte macrophage stimulating factor); and % inh. refers to percent inhibition of the cytokine.

Based on the foregoing, it can be seen that the tested compounds were able to modulate lymphocyte activation induced by T-cell stimulation.

EXAMPLE 7

Anti-Inflammatory Activity on Release of UV-Induced Pro-Inflammatory Mediators on Reconstituted Epidermis The effect of diamines was evaluated for topical anti-inflammatory activity on human epidermal equivalents. Epidermal equivalents (EPI 200 HCF), multilayer and differentiated epidermis consisting of normal, human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm²) with compounds in 70% ethanol/30% propylene glycol vehicle at the indicated concentration 2 hours before exposure to solar ultraviolet light (1000 W-Oriel solar simulator equipped with a 1-mm Schott WG 320 filter; UV dose applied: 70 kJ/m² as measured at 360 nm). Equivalents were incubated for 24 hours at 37° C. with maintenance medium then supernatants were analyzed for IL-1A cytokine release using commercially available kits (Upstate Biotechnology, Charlottesville, Va.). The results are depicted on Table VIII.

TABLE VIII

| Treatment (Dose, as % w/v) | Mean +/− Std Dev of IL-1A Release (ng/ml) | Percent Inhibition of Skin Inflammation |
|---|---|---|
| Untreated, No UV | 115.7 ± 15.2 | — |
| UV, Vehicle Treated | 320.6 ± 35.6 | — |
| UV, Feverfew (1.0%) | 159.0 ± 38.3** | 50.4% |
| UV, Feverfew (0.5%) | 287.4 ± 75.4 | 10.4% |
| UV, THPED (0.5%) | 357.3 ± 92.1 | 0% |
| UV, Feverfew (0.5%) + THPED (0.5%) | 180.0 ± 67.4** | 43.8% |

**Indicates significant difference from UV, Vehicle treated using a student's t-Test with significance set at P < 0.05.

Thus, THPED was found to significantly enhanced the anti-inflammatory activity of Feverfew.

EXAMPLE 8

Reduction of Methyl Nicotinate-Induced Skin Erythema

Methyl nicotinate (methyl 3-pyridinecarboxylate) is a known vasodilator causing an increased cutaneous blood flow upon its application on the skin. See Guy R. H., Arch. Dermatol Res (1982) 273:91-95. In this experiment, between 1-5 mM-solution of methyl nicotinate (Aldrich Chemical, St. Louis, Mo.) was topically applied for 30 sec under occlusion (2.5 cm disk, Hill Top Research Inc, Cincinnati, Ohio) on the volar forearm of 7 volunteers. Formulation placebo or formulation containing Feverfew alone or Feverfew extract plus THPED was topically applied 30 minutes before the methyl nicotinate challenge. Redness was assessed by diffuse reflectance spectroscopy. See Kollias N, et al., Photochem Photobiol. (1992) (56):223-227. An Ocean Optics (Dunedin, Fla.) Diode array spectrophotometer connected to a HP laptop computer through a USB port was used to control the experiment and to collect and analyze the spectral data. An optic fiber bundle was used to conduct the light from the lamp to the skin and transmit the reflectance measurements back from the skin to the spectrophotometer. The results are depicted in Table IX.

TABLE IX

| Treatment (Dose, as % w/v) | Mean +/− Std Dev of Apparent Hemoglobin | Percent Inhibition of Skin Erythema |
|---|---|---|
| Placebo | 0.55 ± 0.18 | — |
| Feverfew (1%) | 0.39 ± 0.26** | 28.9% |
| Feverfew (0.5%) | 0.49 ± 0.20 | 8.7% |
| THPED (2.5%) + Feverfew (0.5%) | 0.40 ± 0.21** | 26.0% |

**Indicates significant difference from Placebo treated using a student's t-Test with significance set at P < 0.05.

These results indicate that THPED potentiated the redness-reducing activity of Feverfew in a methyl nicotinate-induced human redness model

EXAMPLE 9

Clinical Study for Reducing the Appearance of Discoloration and Wrinkles Around the Eye A composition containing 2.5% THPED was compared to a corresponding placebo composition for the reduction of the appearance of discoloration and wrinkles around the eye. 25 subjects were enrolled in the study, with all of the subjects completing the protocol. Table X discloses the formulation of the two compositions.

TABLE X

| Ingredients | Placebo Formulation % WT/WT | THPED Formulation % WT/WT |
|---|---|---|
| Deionized Water | 91.31 | 88.81 |
| PVM/MV Decadiene Crosspolymer | 1.5 | 1.5 |
| Disodium EDTA | 0.1 | 0.1 |
| Sucrose Cocoate | 0.75 | 0.75 |
| PEG-6 Capric/Caprylic Glycerides | 0.75 | 0.75 |
| Hexylene Glycol | 1 | 1 |
| Sodium Hydroxide | 0.59 | 0.59 |
| Talc #2 Guangxi H8162 | 0.5 | 0.5 |
| Nylon 12 | 1 | 1 |
| Silicone Quaternium-13 | 1 | 1 |
| Ethyl Alcohol | 0.5 | 0.5 |
| THPED | — | 2.5 |
| Phenoxyethanol, Methylparaben, Butylparaben, Ethylparaben, and Propylparaben | | |

About 0.47-0.52 g of each composition was applied under one eye of each subject and allowed to dry. Each composition was applied only once to the area for the duration of this study. At baseline and thirty minutes after composition application, a trained grader evaluated the test areas using a ten-point scale, where:

0=Very Poor, Extremely Noticeable, or Severe

10=Excellent, Not At All Noticeable, or None

Table XI illustrates the total percent improvement in responders determined from live grading for each composition.

TABLE XI

| | % Improvement | |
|---|---|---|
| | THPED Composition | Placebo Composition |
| Overall Appearance of Eye | 12.5* | 0.00 |
| Overall Appearance Under Eye | 12.5* | 0.00 |
| Appearance of Dark Circle | 17.26* | 1.09 |
| Intensity of Dark Circle | 17.85* | 0.00 |
| Size of Dark Circle | 19.64* | 0.00 |
| Fine Lines/Wrinkles Under Eye | 33.33* | 2.17 | where, using a two-sample t-test assuming equal variances, the following significance values were calculated: * $p=<0.05$ vs. Placebo The results in Table XI indicate that the composition containing THPED had a rapid, statistically significant effect on the reduction of the appearance of dark circles and wrinkles around the eye.

EXAMPLE 10

Induction of Pigmentation in vitro

THPED was tested for its effect on pigmentation, using melanocytes, DOPA staining and computerized image analysis. THPED was obtained from BASF (Florham Park, N.J.). THPED was dissolved in culture medium and pH was adjusted to neutral (pH 7.2). THPED was assayed at concentrations ranging from 0.05-0.01%.

B16 cells (a murine melanoma cell line) were obtained from American Type Culture Collection (Manassas, Va.). Cells were cultured in Dulbecco's Modified Eagle Medium (DMEM) containing 10% fetal bovine serum (FBS), 4.5 mg/ml glucose, 2 mM L-glutamine, sodium pyruvate, without phenol red (Invitrogen, Carlsbad, Calif.). B16 cells were plated on 12 well tissue culture plates (Corning Costar, San Diego, Calif.), at 40,000 cells per well in the above culture media. Cells were allowed to grow overnight and then treated with various concentrations of THPED at pH 7.2 for total 48 hours. Fresh media containing the experimental treatments were changed once daily.

At the end of the treatment, the cells were washed for 5 minutes, twice, in phosphate-buffered saline (PBS, from Life Technologies, Gaithersburg, Md.), then briefly fixed in 10% buffered formalin (from Sigma St. Louis, Mo.) for 10 minutes, washed three times with PBS and stained with 0.1% L-3,4-Dihydroxyphenylalanine (DOPA, from Sigma, St. Louis, Mo.) in PBS for 2-3 hours at 37° C., followed by three PBS washes. DOPA is a substrate for tyrosinase; therefore an increase in staining represents increased tyrosinase activity and pigment production. Images of DOPA-stained cells were taken using a Leica DMIL microscope (Bannockburn, Ill.) and an OPTRONICS DEI-750 digital camera (Goleta, Calif.). All images were obtained and analyzed with Image Pro Plus 4.0 software (Media Cybernetics, Silver Spring, Md.).

The pigment change was evaluated using the scale defined in Table XII.

TABLE XII

| Score | Description |
|---|---|
| 0 | No change in DOPA staining |
| 1 | Minimal increase in DOPA staining |
| 2 | Moderate increase DOPA staining |
| 3 | Strong increase in DOPA staining |
| 4 | Very strong increase in DOPA staining |

Table XIII represents the overall score in change of pigmentation, as evaluated by DOPA staining, as set forth above, when B16 cells were exposed to THPED (0.05% and 0.025 and 0.01% (w/v)) or forskolin (10 ug/ml, Sigma, St. Louis, Mo.), which is a known pigmentation inducer. This Table demonstrates that THPED treatment unexpectedly resulted in increased tyrosinase activity levels similar to or higher than those produced by forskolin.

TABLE XIII

| | Pigmentation score |
|---|---|
| Control | 0 |
| Forskolin, 10 ug/ml (positive control) | 3 |
| THPED 0.05% | 4 |
| THPED 0.025% | 2 |
| THPED 0.01% | 1 |

EXAMPLE 11

THPED Induces Tyrosinase Activity in vitro

THPED was also tested for its ability to induce tyrosinase activity in B16 cells by spectroscopic measuring of the final product, melanin. B16 cells were treated with THPED at different concentrations at pH 7.2 for 48 hours and cells were then lysed in 250 µl of PBS containing 1% Triton X-100 (Sigma, St. Louis, Mo.). The lysates were collected and centrifuged at 14,000 rpm for 5 minutes at 4° C. to pellet any insoluble material. Lysates (100 µl) were transferred to a 96 well assay plate (Corning Costar, San Diego, Calif.) and mixed with 100 µl of 0.1% (w/v) DOPA in PBS. The absorbance at 490 nm was then monitored from 0 to 12 hours using a VersaMax Plate Spectrophotometer (Molecular Devices, Sunnyvale, Calif.) and SoftMax Pro analytical software (Molecular Devices, Sunnyvale, Calif.). The tyrosinase activities were normalized for total protein using the BioRad Dc Protein Assay (Bio Rad, Hercules, Calif.).

Table XIV shows the results of tyrosinase activity at 3-hours, normalized for their relative controls (untreated B16 cells, normalized to 100%), demonstrating that THPED treatment unexpectedly enhanced tyrosinase activity. This Table demonstrates the specificity of the compositions of this invention in inducing pigmentation (e.g., increasing tyrosianse activity up to 201.90%, which is equivalent to forskolin, a positive control).

TABLE XIV

| Treatments | % tyrosinase activity relative to untreated control |
|---|---|
| Untreated | 100.00 |
| forskolin, 10 µg/ml (positive control) | 202.35 |
| THPED, 0.05% | 201.90 |
| THPED, 0.025% | 167.39 |
| THPED, 0.01% | 104.15 |

EXAMPLE 12

THPED Increases Tyrosinase Protein Levels in vitro

THPED was also tested for its ability to induce tyrosinase protein levels in B16 cells. B16 cells were treated with THPED at different concentrations at pH 7.2 for 48 hours and cells were then lysed in 250 µl of PBS containing 1% Triton X-100. B16 cell lysates containing 3.7 µg of protein (for tyrosinase protein analysis) and 1.2 µg of protein (for β-Actin protein analysis) were electrophoresed on 4-20% Tris-Glycine SDS PAGE minigels (Invitrogen, Carlsbad, Calif.), transferred onto PVDF membrane (Bio Rad, Hercules, Calif.), and probed with antibodies for Tyrosinase (1:200 in PBS+0.2% Tween 20+5% BSA, obtained from Santa Cruz Biotechnology, Inc., Santa Cruz, Calif.) and β-Actin (1:2000 in PBS+0.2% Tween 20+5% BSA, obtained from Sigma, St. Louis, Mo.). Protein expression of tyrosinase and β-Actin were analyzed using ECL reagent and Hyperfilm ECL obtained from Amersham (Piscataway, N.J.). The film was developed using a Konica SRX-101A Processor (East Orange, N.J.).

Table XV shows tyrosinase protein levels, normalized to β-Actin control, following the different treatments. Tyrosinase protein level in untreated B16 cells was normalized to 1. Table XV demonstrates that THPED treatment increased tyrosinase protein levels. This Table demonstrates the specificity of the compositions of this invention in inducing pigmentation (e.g., increasing tyrosinase protein level up to 36 fold relative to PBS treated cells, which is equivalent to forskolin (34 fold, positive control).

TABLE XV

| Treatment | Relative increase in tyrosinase protein |
|---|---|
| Control (PBS treated) | 1 |
| Forskolin, 20 µg/ml | 34 |
| THPED, 0.05% | 36 |
| THPED, 0.025% | 25 |
| THPED, 0.01% | 3 |

EXAMPLE 13

Treatment of Acne Disorders

Acne disorders are often classified as noninflammatory or inflammatory types. Noninflammatory acne is characterized by closed comedones (whiteheads) and open comedones (blackheads), consisting of compact masses of keratin, sebum, and bacteria which dilate the follicular duct. A comedone forms when a pilo-sebaceous duct is obstructed and/or when there is increased production of sebum by a sebaceous gland. Formation of the comedone can be followed by inflammation, resulting from bacterial proliferation and/or overproduction of sebum. Typically, the bacteria are anaerobic bacteria such as *Propionibacteria* (*P. acnes*). Inflammatory acne is characterized by papules (pimples), pustules, and nodulocystic lesions which may lead to scarring. Several factors are believed to play important roles in the pathogenesis of acne including: sebum production, hormonal stimulation, plugged pores, and skin pathogens. Sebum levels are increased in subjects with acne by approximately 70% compared to sebum levels of control subjects.

Human sebum differs in its composition from other mammals. The main lipids in human sebum are triglycerides, wax esters, and squalene (Greene, et al. JID 54, 240-247, 1970). Squalene, for instance is not found in many mammals. Triglyceride, which is a major component of human sebum, is poorly represented in other species and in many (e.g. chimpanzee) appears to be. totally absent (Thody, A. J., Shuster, S., Physiolog. Rev. 69, 383-415, 1989). Squalene can be further oxidized to Squalene monohydroperoxide (Sq-OOH), which is the initial product of ultraviolet-peroxidation. This can lead to comedone formation, initiate an inflammatory response, cytotoxicity and comedogenicity (Chiba et al J Biochem Mol Toxicol. 2001; 15(3):150-158). Therefore decreasing squalene formation in sebum may lead to decreased comedone formation, and the appearance of acne including papules (pimples), pustules, and scarring. However, the main lipids in human sebum also can function to maintain skin hydration as shown by a correlation between sebum content and water content of the skin (Aisen E et al., Acta Derm Venereol. (1997) 77:142-143). Various approaches have been tried to reduce sebum production. For example, topical retinoids have been shown to reduce the synthesis of the main lipids in human sebum (Stewart M E et al., J Invest Dermatol. (1984) 82:74-78); however, non-selective suppression of sebum can lead to dry skin (Shalita A R, et al., Clin Ther. (2004) 26:1865-1873).

The ability of THPED to selectively affect the content of squalene present in human sebum without affecting other components of sebum was illustrated by its ability to selectively reduce the content of squalene present in human skin using the following assay.

The Methods used are as described previously by Pappas et al. (J Invest Dermatol. 2002 January; 118(1):164-171). In summary, samples of facial skin (otherwise to be discarded) were obtained from female patients 45-65 years of age. The subjects were healthy females without a history of retinoid or laser treatment or chemotherapy. The specimens were obtained from facial lift surgery within 5 hours from the end of the surgery. Two mm biopsy punches were taken from tissues rich in sebaceous glands and cultured in serum free medium. The medium consisted of DMEM and F12 (3:1) (Gibco San Diego, Calif.) as described previously (Guy and Kealy, Dermatology. 1998; 196(1):16-20) containing, L-glutamine, penicilin-streptomycin, sodium Pyruvate, a selenium-insulin-transferrin mixture, and trace elements (Gibco San Diego, Calif.) and 3,3,5-triiodo-L-thyronine (Sigma, St Louis, Mo.). Finally, prior to incubation of biopsies, the concentration of THPED was adjusted to 25 µM and C14-labelled acetate was added (2 µCi/ml).

For each experimental point, 5 biopsy punches were homogenized in 2 ml of $CHCl_2$:MeOH (2:1) until a milky homogenate was obtained without the presence of visual debris. The homogenate was transferred to a glass tube containing 1 ml of 0.88% potassium chloride. The homogenizer was then rinsed with 2 mls of the extraction solvent twice, and these washes were added to the combined extract. After phase separation, the aqueous phase was removed and discarded while the remaining total organic extract was evaporated under a gentle stream of argon prior to HPTLC analysis.

The lipid components extracted from the explanted glands were analyzed by chromatographic separation on 10×20 cm Whatman HPTLC Silica G plates that had been previously charged with chloroform, heated in a vacuum oven at 105° C. for 30 min and cooled to room temperature in a dessicator. After spotting the lipids that were dissolved in CHCl3:MetOH (2:1), the plates were developed three times, as previously reported (3), as follows: 1) phase Hexane to the top, 2) Toluene to the top and 3) Hexane/Ether/Acetic Acid (70:30:1) 10 cm from the top. Between each mobile phase, a 15 min drying time at room temperature in a standard fume hood was carried out to ensure complete evaporation of the solvent. Squalene, waxes and sterol esters are separated during the first two phases while the various polar lipids are resolved during the third phase.

Biopsy punches from human facial skin in the presence of THPED demonstrated decreased accumulation of squalene without substantially affecting other components of sebum such as Triglycerides. Results from two different experiments comprising two different donors are summarized in the following Table XVI:

TABLE XVI

|  | Inhibition of Squalene accumulation, (Percent of Vehicle Treated) | Inhibition of Triglyceride accumulation, (Percent of Vehicle Treated) |
| --- | --- | --- |
| THPED (25 um) | 44.0% | 2.65% |

Unlike compounds which decrease or suppress sebum production by interfering in synthesis of the main lipids in human sebum (triglycerides, wax esters and squalene) THPED was found effective in selectively reducing Squalene formation without affecting other components of sebum. The main lipids in human sebum function to maintain the lipid barrier in skin, regulating the water content of the skin and thus keeping skin from becoming dry and cracked. The decrease in squalene by THPED could decrease comedone formation, and the appearance of acne including papules (pimples), pustules, and scarring.

EXAMPLE 14

Clinical Study Evaluation for Reduction of Pore Size in Skin

A composition containing 2.5% THPED was compared to a corresponding placebo composition for the reduction of pore size on facial skin. 31 subjects were enrolled in the study, with all of the subjects completing the protocol. Table XVII discloses the formulation of the two compositions.

TABLE XVII

| Ingredients | THPED Formulation % WT/WT | Placebo Formulation % WT/WT |
| --- | --- | --- |
| Deionized Water | 88.81 | 91.31 |
| PVM/MV Decadiene Crosspolymer | 1.5 | 1.5 |
| Disodium EDTA | 0.1 | 0.1 |
| Sucrose Cocoate | 0.75 | 0.75 |

TABLE XVII-continued

| Ingredients | THPED Formulation % WT/WT | Placebo Formulation % WT/WT |
|---|---|---|
| PEG-6 Capric/Caprylic Glycerides | 0.75 | 0.75 |
| Hexylene Glycol | 1 | 1 |
| Sodium Hydroxide | 0.59 | 0.59 |
| Talc #2 Guangxi H8162 | 0.5 | 0.5 |
| Nylon 12 | 1 | 1 |
| Silicone Quaternium-13 | 1 | 1 |
| Ethyl Alcohol | 0.5 | 0.5 |
| THPED | 2.5 | — |
| Phenoxyethanol, Methylparaben, Butylparaben, Ethylparaben, and Propylparaben | 1 | 1 |

About 0.45-0.52 g of each composition was applied on one side of the face for each subject and allowed to dry. Each composition was applied only once to the area for the duration of this study. At baseline and 45 minutes after composition application, parallel-polarized digital images were taken of the entire face to document changes observed in pore size. Pore Size Reduction was evaluated using computer analysis of Parallel-Polarized images of the face.

Computer analysis of parallel-polarized images demonstrated: that 74.2% of subjects treated with THPED obtained a reduction in pore size. THPED treatment resulted in a 19.4% greater pore reduction response than the placebo alone.

Table VIII illustrates the total percent pore reduction in the subject responders to the THPED treatment over the Placebo.

TABLE VIII

| | THPED |
|---|---|
| % Of Pore Size Reduction over Placebo | 7.11%* | where, using a paired t-test, the following significance values were calculated:
*p = <0.01 vs. Placebo Table XIX illustrates percent of subjects that observed a measurable reduction of pore size.

TABLE XIX

| | % Of Subjects with Pore Reduction | |
|---|---|---|
| | THPED | Placebo |
| % Of Subjects | 74.2% * | 54.8% |

Thus, THPED was found to inhibit reduce the appearance of pores in 74.2% of the subjects.

What is claimed is:

1. A method of treating acne, said method comprising administering to skin in need of such treatment a composition comprising (A) from about 0.5 to about 3% by wt. of at least one compound of the formula I:

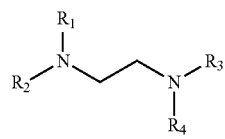

(I)

wherein R1, R2, R3, and R4 independently, are selected from the group consisting of $C_1$-$C_3$ alkyl, $C_1$-$C_3$ hydroxyalkyl an enantiomer thereof, or a diastereoisomer thereof or a cosmetically acceptable salt thereof, and (B) from about 0.01 to about 5% by wt. of salicylic acid.

2. A method of claim 1, wherein said composition comprises a compound of the following formula:

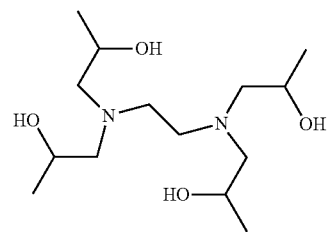

or a cosmetically acceptable salt thereof.

* * * * *